United States Patent
de Maat et al.

(10) Patent No.: US 7,867,519 B2
(45) Date of Patent: Jan. 11, 2011

(54) METHOD FOR THE ACCELERATION OR DECELERATION OF ANGIOGENESIS USING FIBRIN MATRIX FORMED FROM INCREASED OR DECREASED HMW/LMW FIBRINOGEN RATIO

(75) Inventors: Monica Petronella Maria de Maat, Rotterdam (NL); Pieter Koolwijk, Alkmaar (NL)

(73) Assignee: Nederlandse Organisatie Voor Toegepast-Natuurwetenschappelijk Onderzoek TNO, Delft (NL)

( * ) Notice: Subject to any disclaimer, the term of this patent is extended or adjusted under 35 U.S.C. 154(b) by 677 days.

(21) Appl. No.: 10/511,700

(22) PCT Filed: Apr. 7, 2003

(86) PCT No.: PCT/NL03/00293

§ 371 (c)(1),
(2), (4) Date: Oct. 15, 2004

(87) PCT Pub. No.: WO03/087160

PCT Pub. Date: Oct. 23, 2003

(65) Prior Publication Data

US 2005/0181972 A1    Aug. 18, 2005

(30) Foreign Application Priority Data

Apr. 18, 2002    (NL) .................................. 1020426

(51) Int. Cl.
*A61K 35/16* (2006.01)
*A61K 38/00* (2006.01)

(52) U.S. Cl. .......................................... 424/530; 514/12
(58) Field of Classification Search ....................... None
See application file for complete search history.

(56) References Cited

U.S. PATENT DOCUMENTS 6,946,140 B1 * 9/2005 Clark et al. .................. 424/422

FOREIGN PATENT DOCUMENTS

| EP | 1 142 581 A2 | 11/1991 |
| WO | 98 55140 A1 | 12/1998 |
| WO | 00/62833 * | 10/2000 |
| WO | 00 72852 A1 | 12/2000 |

OTHER PUBLICATIONS

Gunji et al., "Role of fibrin coagulation in protection of murine tumor cells from destruction by cytotoxic cells", Cancer Research 48 (18): 5216-5221 (1988).*

Vaage et al., "Normal inhibition of mammary tumor metastasis in C3H-He mice", Clinical and Experimental Metastasis 9 (3): 273-282 (1991).*

Atagi et al., "Inhibition by fibrin coagulation of lung cancer cell destruction by human interleukin-2-activated killer cells", Japanese Journal of Cancer Research 83 (10): 1088-1094 (1992).*

Holm et al., :Purification and characterization of 3 fibrinogens with different molecular weights obtained from normal human plasma, Thrombosis Research 37: 165-176 (1985).*

Hasegawa et al., "Location of the Binding Site "b" for Lateral Polymerization of Fibrin", Thrombosis Research 57: 183-187 (1990).*

Smith et al., "The Role of Putative Fibrinogen A alpha-, B beta-, and gammaA-chain Integrin Binding Sites in Endothelial Cell-mediated Clot Retraction", Journal of Biological Chemistry 272 (35): 22080-22085 (1997).*

Falls et al., "Resistance of gamma A/gamma" Fibrin Clots to Fibrinolysis, Journal of Biological Chemistry 272 (22): 14251-14256 (1997).*

Kaijzel et al., "Molecular weight fibrinogen variants determine antiogenesis rate in a fibrin matrix in vitro and in vivo", J. Thrombosis and Haemostasis 4: 1975-1981 (2006).*

Zhang et al., "Ocular neovascularization: Implication of endogenous angiogenic inhibitors and potential therapy", Progress in Retinal and Eye Research 26: 1-37 (2007).*

Hallemeesch, Marcella M., et al.: "The turnover rate of HMW fibrinogen to LMW fibrinogen determines the plasma profile of these proteins"; FASEB Journal, Mar. 22, 2002 (ISSN 0892-6638); XP-002226013 © BIOSIS / BIOSIS.

Collen, Annemie, et al.: "Aberrant fibrin formation and cross-linking of fibrinogen Nieuwegein, a variant with a shortened Alpha-chain, alters endothelial capillary tube formation", Blood, Feb. 15, 2001, vol. 97, No. 4; XP-002226021; © by the American Society of Hematology (pp. 973-980).

* cited by examiner

*Primary Examiner*—Sandra Saucier
(74) *Attorney, Agent, or Firm*—Norris McLaughlin & Marcus, P.A.

(57) ABSTRACT

A method for modifying the properties of a fibrin matrix relative to growth and ingrowth of cells, wherein for forming the fibrin matrix a fibrinogen is used consisting of a selected fibrinogen variant or a fibrinogen enriched or depleted in a selected fibrinogen variant. In particular, the use of high-molecular weight (HMW) fibrinogen leads to a fibrin having accelerated angiogenesis properties, while the use of low-molecular weight (LMW and/or LMW') fibrinogen leads to fibrin having decelerated angiogenesis properties. The use of HMW fibrinogen when setting up angiogenesis tests results in that the tests require less time. Fibrin sealants on the basis of HMW fibrinogen can be used for burns, to promote wound healing or to inhibit scar tissue. Fibrin sealants on the basis of LMW or LMW' fibrinogen are useful to inhibit adhesions and tumor growth, for instance after surgical operations.

13 Claims, 5 Drawing Sheets

100% HMW

90% HMW : 10% LMW

80% HMW : 20% LMW

60% HMW : 40% LMW

Microvascular endothelial cells on fibrin (48 h):

100% HMW

70% HMW + 30% LMW

60% HMW + 40% LMW

Human Smooth Muscle Cells on fibrin (48h):

100% HMW

70 % HMW + 30% LMW

50% HMW + 50% LMW

Human fibroblasts on fibrin

100% HMW

70% HMW + 30% LMW

METHOD FOR THE ACCELERATION OR DECELERATION OF ANGIOGENESIS USING FIBRIN MATRIX FORMED FROM INCREASED OR DECREASED HMW/LMW FIBRINOGEN RATIO

BACKGROUND

Fibrinogen

Fibrinogen is a soluble plasma protein which plays an important role in blood clotting. The fibrinogen molecule, having a molecular weight of about 340 kDa, circulates in plasma in a concentration of 2-4 g/l. It has an elongate structure and is 475 Å long and 8-15 Å in diameter, having a dual symmetry axis through the center of the molecule. The molecule consists of two sets of three polypeptide chains, the Aα, Bβ and γ chains, which are mutually connected by disulfide bridges. Each molecule contains at the terminal ends two D-domains, which are connected through coiled-coil segments with the central E-domain. The Aα-chain contains 610, the Bβ-chain 461 and the γ-chain 411 amino acids.

The soluble fibrinogen is converted at the end of the clotting cascade into insoluble fibrin by thrombin, whereafter a network of fibrin threads is formed, which constitutes the basis of a blood clot. First, by thrombin, two polypeptides are split off from the N-terminus of the fibrinogen molecule, next protofibrils are formed through rapid non-covalent binding of the fibrin monomers. These protofibrils are formed from a chain of alternately arranged molecules, and through lateral binding a fibrin network is formed. Finally, the network is stabilized by factor XIIIa-stimulated crosslinking.

Heterogeneity

There are a large number of patients with dysfibrinogenemia known, whereby functional parts of the fibrinogen molecule are gone, or have so changed as to have acquired a different function. These changes lead to a wide range of variations in fibrinogen function and fibrinogen structure, and patients with a dysfibrinogenemia also exhibit a variable clinical picture, with both bleeding and clotting tendencies. The cause of dysfibrinogenemia are mutations in the gene for fibrinogen and therefore 50% (in a heterozygote) or 100% of the fibrinogen (in a homozygote) is deviant.

In addition to these severe and rare variations in the fibrinogen molecule, there is a milder genetic form of variation in the fibrinogen. In a large part of the population, genetic polymorphisms occur, which, however, have only a mild or no effect on fibrinogen function. To be mentioned as examples are the T/A312 polymorphism in the fibrinogen alpha gene and the R/K448 polymorphism in the fibrinogen beta gene.

In addition to that, the fibrinogen also occurs in a large number of variants within each individual, an estimate being that in each individual about $10^6$ different fibrinogen molecules circulate. These variants too only give mild differences in fibrinogen function and fibrinogen structure and they account for just a small portion of the total fibrinogen (mostly not more than a few percents). There exist, for instance, forms having different glycosylations and phosphorylations and also the C-terminal end of the alpha chain of fibrinogen may be partly broken down in vivo (see Table for a number of examples of fibrinogen variants). These different forms of fibrinogen each have their typical characteristics, whereby the basic function, forming a fibrin network, remains intact, but the fibrin networks formed may differ in characteristics. As a result of the heterogeneity, there is variation in inter alia the binding properties, for instance 1) of enzymes and proteins that play a role in fibrinolysis, or 2) binding of factor XIII, which influences the stability of the fibrin, or 3) variation in rate and extent of lateral growth of the fibrin, resulting in fibrin having e.g. thinner fibers, more branches, and the like.

One of the known variants is γ' (gamma') which is formed through alternative processing of the primary mRNA transcript. About 8% of the total γ-chains is of this form. The γ' chain consists of 427 amino acids and the four C-terminal amino acids (AGDV) have been replaced therein with an anionic sequence of 20-amino acids that contains 2 sulphated tyrosines. The fibrinogen γ' chain binds plasma factor XIII, but does not bind to the platelet fibrinogen receptor IIbβ3, this in contrast to the normal γ chain whose C-terminal sequence (400-411) plays a critical role in regulating platelet aggregation.

Another variant of fibrinogen is Fib420, which has a molecular weight of 420 kDa. In healthy persons, this variant accounts for about 5% of the total circulating fibrinogen. Through alternative splicing of the a-chain transcript an extra open reading frame is included, so that an Aα-chain arises which is extended on the carboxyterminal side by circa 35% (847 amino acids). The additional length of Aα-chain has a nodular structure and as far as known, no fibrinogen molecules occur that have this additional piece on just one Aα-chain. This fibrinogen variant Fib420 might be less sensitive to degradation and could have an effect on the clot structure.

Another cause of molecular heterogeneity in the fibrinogen molecules is a partial degradation of the carboxyterminal part of the Aα-chain, which results in three forms of fibrinogen having a different molecular weight. Fibrinogen is synthesized in the high-molecular weight form (HMW) having a molecular weight of 340 kDa, with Aα-chains that contain 610 amino acids. The degradation of one of the Aα-chains gives the low-molecular weight form (LMW)(MW=305 kDa) and thereafter also the other chain is affected and the LMW' form (270 kDa) is created. In blood of healthy persons, about 70% of the fibrinogen occurs in the HMW-form, 26% in the LMW form and 4% in the LMW' form. The enzyme that takes care of the conversion of HMW to LMW and LMW' has not been identified to date, but a number of enzymes (for instance elastin and plasmin) have already been precluded. The LMW fibrinogen clots slightly more slowly than HMW fibrinogen and the LMW' form clots most slowly. Also the ADP-induced aggregation of platelets is less with LMW than with HMW fibrinogen.

Angiogenesis

Angiogenesis, the outgrowth of new blood vessels from existing blood vessels is an essential process during the embryonal development, and in adults normally occurs only in the female reproductive system (in the formation of the corpus luteum and the placenta) and in wound healing. In addition, angiogenesis is also associated with many pathological conditions, such as chronic inflammations, rheumatoid arthritis, tumors and retinopathy in diabetics. The major difference between these two forms of angiogenesis is that in "pathologic angiogenesis" the process is accompanied by vascular leakage, the infiltration of inflammation cells, such as monocytes and lymphocytes, and the presence of fibrin. The fibrin, which forms after a wounding of blood vessels or through leakage of fibrinogen from the plasma to the tissues, forms a temporary matrix which not only functions as a barrier to prevent much blood loss, but is also a matrix in which new blood vessels can invade and grow during e.g. wound healing.

The angiogenesis process is set in motion after activation of the endothelial cells by angiogenic growth factors and cytokines. These proceed to produce proteolytic enzymes that are needed for the degradation of the basal membrane under the endothelial cells. After this follows migration of the endothelial cells to the subjacent interstitial tissue/matrix, followed by a proliferation of the endothelial cells. At the end of the angiogenesis process, it is necessary, after the formation of a lumen between the endothelial cells, for the new blood vessel to be stabilized by the deposition of a new basal membrane and the entering into a close interaction between endothelial cells and pericytes.

The initiation and the progress of the angiogenesis is closely controlled by angiogenic growth factors and cytokines, but can only take place when it is done in the proper (temporary) matrix. If this is not the case, the endothelial cells become insensitive to the stimulation, or respond to the stimulation but subsequently go into apoptosis. The interaction of the endothelial cells with the fibrin matrix by means of cellular receptors, such as integrins, determines to a large extent the response of the cells to the stimulation. These adhesion molecules not only provide for the adhesion of the cells to the matrix, but also pass on biochemical signals to the cell. Through these biochemical signals, the cell obtains information about the matrix composition and the "responsiveness" of the cell towards particular angiogenic factors and cytokines is influenced.

A controlled invasion of the temporary matrix by the endothelial cells is also very important for the process of angiogenesis during wound healing. An unduly fast ingrowth can lead to an unduly fast degradation of the matrix and hence an inadequate wound healing. In addition, an unduly slow ingrowth of blood vessels can lead to scar tissue. The ingrowth of the endothelial cells in the temporary matrix is therefore strongly regulated by a number of proteolytic enzymes with their receptors and a number of inhibitors. Examples include the enzymes of the urokinase-type plasminogen (u-PA)/plasmin system and the different matrix metalloproteases (MMPs). Especially the first system plays an important role in the formation of blood vessels in the temporary fibrin matrix.

Fibrinogen in Angiogenesis

Research into determinants of angiogenesis has focused on the optimization of the added (growth) factors. The role of normal variation in the fibrinogen molecule has not been involved in it yet, though some attention has been paid to the effects of fibrinogen$_{Nieuwegein}$, a rare mutation in the fibrinogen which causes albumin to be bound covalently to the fibrinogen, which gives steric hindrance in the formation of the fibrin clot. This fibrinogen also exhibits a strongly prolonged clotting time and gives very clear clots (Collen et al, Blood 97: 973-980, 2001).

BRIEF SUMMARY OF THE INVENTION

We have made extensive investigations into the influence that fibrinogen exerts on the growth of cells and especially the formation and ingrowth of cells and blood vessels (angiogenesis) in the fibrin matrix formed from the fibrinogen. In particular, we investigated whether any differences arose between normal naturally occurring variants of fibrinogen.

Surprisingly, we found that different variants of fibrinogen exert a different influence on cell growth and especially the formation and ingrowth of small blood vessels. More in particular we established that LMW fibrinogen, compared with total fibrinogen which is essentially a mixture of HMW, LMW, and LMW' fibrinogen, gives a reduced cell and vessel ingrowth. This is also true of LMW' fibrinogen. HMW fibrinogen, by contrast, is conducive to cell growth and leads to an increased cell and vessel ingrowth, compared with total fibrinogen.

This finding can be utilized in various ways and for different purposes, as will be set out in the following detailed description of the invention.

DETAILED DESCRIPTION OF THE INVENTION

Figure 1:
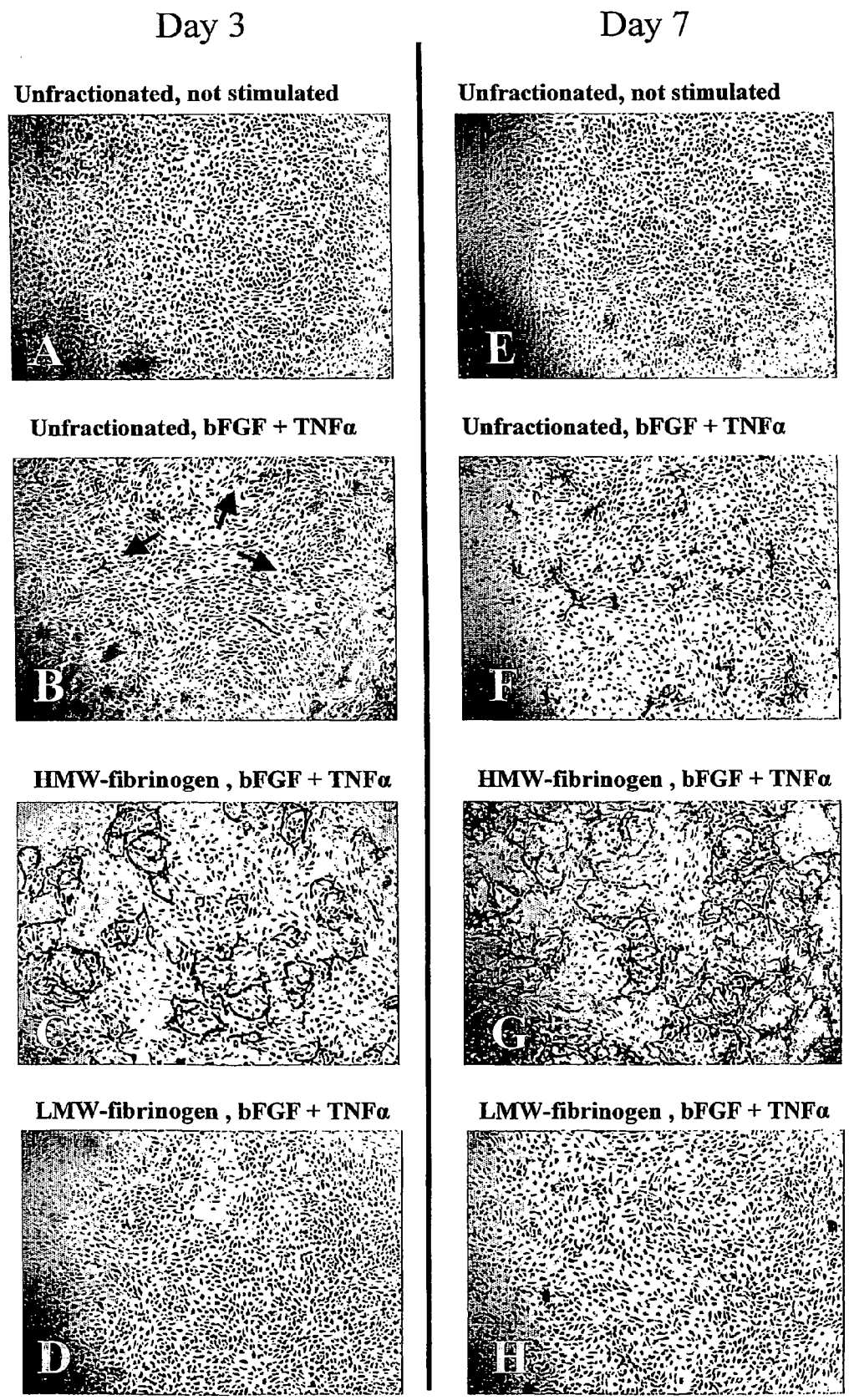
FIG. 1 contains photos A-H, showing the results after, respectively, 3 days (photos A-D) and 7 days (photos E-H) of experimenting, whereby human microvascular endothelial cells (hMVEC) were seeded on a three-dimensional fibrin matrix, made of unfractionated fibrinogen (photos A, B, E and F), HMW fibrinogen (photos C and G) or LMW fibrinogen (photos D and H) and not stimulated (photos A and E) or stimulated with a combination of bFGF and TNFα (photos B-D and F-H). The photos are representative of 3 different experiments.

The present invention provides a method for modifying the properties of a fibrin matrix with respect to growth and ingrowth of cells, wherein for the formation of the fibrin matrix a fibrinogen is used that consists of a selected fibrinogen variant or a fibrinogen that is enriched or depleted in a selected fibrinogen variant.

As regards the properties to be modified of the fibrin matrix with respect to growth and ingrowth of cells, various properties can be considered. Preferably, this involves properties that concern the growth and ingrowth of blood vessels, such as more particularly angiogenesis properties. To be considered here especially is a modification that accelerates angiogenesis or a modification that decelerates angiogenesis.

"Fibrinogen variant" is herein understood to mean especially a variant of fibrinogen occurring in normal persons.

'Normal persons' is understood to mean healthy persons that possess normal fibrinogen. To be considered in particular is a normal fibrinogen variant selected from the group consisting of HMW fibrinogen, LMW fibrinogen, LMW' fibrinogen, Fib420 fibrinogen and gamma' fibrinogen. However, also other natural or artificial variants of fibrinogen, such as variants due to a polymorphism, e.g. T/A312 fibrinogen and R/K448 fibrinogen, variants with deviant phosphorylation and/or glycosylation, and, for instance, variants truncated artificially by means of recombinant DNA technology, can be used to modify the properties of the fibrin matrix in respect of cell growth and cell ingrowth. Examples of artificially truncated variants include LMW-like variants, which, just like LMW fibrinogen, lack a part of one of the A$\alpha$-chains, but a greater or smaller part than the natural LMW fibrinogen. Another example concerns LMW'-like variants, of which both A$\alpha$-chains, just as in LMW' fibrinogen, are lacking in part but where the lacking parts are greater or smaller than in natural LMW' fibrinogen.

The invention concerns not only the use of a selected fibrinogen variant that has been recovered from natural fibrinogen by isolation, but also the use of a selected fibrinogen variant which has been produced by means of recombinant DNA technology. The recombinant production of fibrinogen has been described in the literature, e.g. in the American patent specification U.S. Pat. No. 6,037,457.

In a preferred embodiment of the invention, for the formation of the fibrin matrix a fibrinogen is used that consists of HMW fibrinogen or of a mixture of fibrinogen variants that is enriched in HMW fibrinogen or depleted in LMW fibrinogen and/or LMW' fibrinogen. In this embodiment, the fibrin matrix formed leads to accelerated angiogenesis.

In another preferred embodiment of the invention, for the formation of the fibrin matrix a fibrinogen is used that consists of LMW fibrinogen or of a mixture of fibrinogen variants that is enriched in LMW fibrinogen or depleted in HMW fibrinogen. In this embodiment, the fibrin matrix formed leads to decelerated angiogenesis.

In yet another preferred embodiment of the invention, for the formation of the fibrin matrix a fibrinogen is used that consists of LMW' fibrinogen or of a mixture of fibrinogen variants that is enriched in LMW' fibrinogen or depleted in HMW fibrinogen. In this embodiment too, the fibrin matrix formed leads to decelerated angiogenesis.

In yet another embodiment of the invention, for the formation of the fibrin matrix a fibrinogen is used that consists of Fib420 fibrinogen or of a mixture of fibrinogen variants that is enriched in Fib420 fibrinogen.

In yet another embodiment of the invention, for the formation of the fibrin matrix a fibrinogen is used that consists of gamma' fibrinogen or of a mixture of fibrinogen variants that is enriched in gamma' fibrinogen. When herein reference is made to a mixture of fibrinogen variants that is enriched or depleted in a selected fibrinogen variant, this is understood to refer to an enrichment or depletion with respect to the mixture of which natural fibrinogen consists. A mixture that is enriched in HMW fibrinogen or depleted in LMW fibrinogen is therefore understood to refer to a mixture that comprises, respectively, significantly more than 70% HMW fibrinogen (preferably more than 80%, more preferably more than 90% HMW fibrinogen), or significantly less than 26% LMW fibrinogen (preferably less than 20%, more preferably less than 10% LMW fibrinogen). Conversely, a mixture that is enriched in LMW fibrinogen or depleted in HMW fibrinogen is understood to refer to a mixture that comprises, respectively, significantly more than 26% LMW fibrinogen (preferably more than 40%, more preferably more than 50% LMW fibrinogen), or significantly less than 70% HMW fibrinogen (preferably less than 60%, more preferably less than 50% HMW fibrinogen). A mixture that is enriched, or depleted, in LMW' fibrinogen, is understood to refer to a mixture that comprises, significantly more, and significantly less, respectively, than 4% LMW' (preferably more than 10% LMW' fibrinogen, respectively preferably less than 2%, more preferably less than 1% LMW' fibrinogen). A mixture that is enriched or depleted, respectively, in Fib 420 fibrinogen is understood to refer to a mixture that comprises significantly more, respectively significantly less than 5% Fib420 fibrinogen (preferably more than 10%, more preferably more than 20% Fib420 fibrinogen, or preferably less than 2%, more preferably less than 1% Fib420 fibrinogen). A mixture that is enriched, or depleted, in gamma' fibrinogen, is understood to refer to a mixture that comprises significantly more, and significantly less, respectively, than 8% gamma' fibrinogen (preferably more than 15%, more preferably more than 20% gamma' fibrinogen, or preferably less than 4%, more preferably less than 2% gamma' fibrinogen).

The term "fibrin matrix" as used herein has a broad meaning. Usually, the fibrin matrix, as is the case by nature, will contain, in addition to the fibrin, which in the form of a network of fibrin threads forms the basis of the fibrin matrix, also contain other substances. The term "fibrin matrix", however, is understood to refer not only to fibrin matrices more or less natural qua composition, but also to artificial fibrin matrices exhibiting a ratio of the components deviating from the natural composition, such as fibrin and collagen.

The invention relates to in vitro as well as in vivo processes. According to one of the preferred embodiments, the fibrin matrix is formed in vitro, the fibrin matrix being formed by converting the fibrinogen by means of a suitable enzyme, such thrombin, and optionally factor XIIIa and $CaCl_2$, into fibrin. The thus obtained fibrin matrix may, for instance, be used in an angiogenesis test. Such a test may be directed to new scientific insights, or be used to test substances for their possible action or effect in angiogenesis. Mostly, it will be favorable if the ingrowth of cells and blood vessels occurs fast, which according to the invention can be obtained by using a fibrinogen variant leading to a fibrin matrix with accelerated angiogenesis characteristics, as is the case when using HMW fibrinogen or a mixture of fibrinogen variants enriched in HMW fibrinogen.

According to another preferred embodiment, the invention relates to a method in which the fibrin matrix is formed in vivo, the fibrinogen, optionally together with a suitable enzyme, such as thrombin, and optionally factor XIIIa and $CaCl_2$, being applied in the place where the formation of a fibrin matrix takes place (topical administration). For instance, the fibrinogen is applied to inhibit or prevent tumor growth, cicatrization, adhesions and the like, or to promote the healing of burns and other wounds.

The effect on cicatrization can be explained as follows. In case of vessel wall damage, fibrin forms the network stopping a bleeding. The fibrin network then functions as matrix for fibroblasts, endothelial cells and endothelial precursor cells which begin to form the scar tissue. The velocity of ingrowth of the cells (=angiogenesis) codetermines the degree of cicatrization. The application to the wound of a layer of fibrinogen "sealant" of a specific composition will influence the velocity of angiogenesis and thus the degree of cicatrization. For instance, an HMW-enriched sealant will lead to faster vessel ingrowth and less scar tissue.

As far as adhesions are concerned, these often occur after surgical operations. Up to 80-95% of the patients undergoing an abdominal operation have trouble with adhesions to a greater or lesser degree. The adhesions may consist of a thin film of connective tissue, or a thick fibrous layer with blood vessels, or a direct contact between organ surfaces. Adhesions may give different complications, including infertility with women or obstruction of the intestine. Adhesions are caused not only by surgical operations, but also by, for instance, infections, inflammation diseases, endometriosis, etc. The first step in the process comprises the formation of fibrin. This must be dissolved again in time by the fibrinolytic system. If the fibrin does not dissolve in time, fibrous adhesions may develop. The fibrin is actually a matrix for the ingrowth of fibroblasts, and this subsequently leads to collagen deposition and vessel ingrowth and may thus lead to permanent adhesions. The introduction of a fibrinogen in which the ingrowth of vessels and the ingrowth of fibroblasts is decelerated, will help prevent the occurrence of adhesions. Also, in surgical operations, a layer of a fibrinogen preventing adhesions could be directly applied to the respective organs.

In addition to topical administration, however, an in vivo application is also possible, in which the fibrinogen is systemically administered, for instance by means of an intravenous injection or infusion, or in any other method of administration suitable for the intended object.

Another possibility is that the fibrin matrix is formed in vivo, the selected fibrinogen variant being formed in situ from another fibrinogen variant. An example of such an alternative approach is stimulation of the conversion of HMW fibrinogen into LMW fibrinogen, for instance within the scope of a treatment of post-thrombotic syndrome (open leg). This conversion takes place by nature under the influence of an enzyme or combination of enzymes. This may be used for extra stimulation thereof, for instance by increasing the expression of the enzyme or by administering the enzyme itself or an agonist thereof.

The present invention is also embodied in a pharmaceutical composition, comprising fibrinogen and a pharmaceutically acceptable carrier, the fibrinogen consisting of a selected fibrinogen variant or a fibrinogen enriched or depleted in a selected fibrinogen variant.

The pharmaceutical composition may optionally also contain other components, such as factor XIIIa and $CaCl_2$, together with or separated from the fibrinogen. Also, the pharmaceutical composition may contain a suitable enzyme, such as thrombin, separated from the fibrinogen. "Suitable enzyme" is understood to refer to an enzyme capable of converting fibrinogen into fibrin. As this conversion may normally not take place until during and after application at the destination, this enzyme must only then, during application, be combined with the fibrinogen.

In a specific embodiment of the invention, a pharmaceutical composition is involved, in which the fibrinogen consists of HMW fibrinogen or of a mixture of fibrinogen variants enriched in HMW fibrinogen or depleted in HMW and/or LMW' fibrinogen. Such a pharmaceutical composition is suitable for promoting wound healing, inhibiting or preventing cicatrization or treating burns.

According to another preferred embodiment of the invention, a pharmaceutical composition is involved, in which the fibrinogen consists of LMW en/of LMW' fibrinogen or of a mixture of fibrinogen variants enriched in LMW and/or LMW' fibrinogen or depleted in HMW fibrinogen. Such a pharmaceutical composition is suitable for inhibiting or preventing tumor growth or adhesions.

The present invention also relates to a test kit, comprising components for forming a fibrin matrix, including fibrinogen, the fibrinogen consisting of a selected fibrinogen variant or a fibrinogen enriched or depleted in a selected fibrinogen variant.

Preferably, a test kit is involved, in which the fibrinogen consists of HMW fibrinogen or of a mixture of fibrinogen variants enriched in HMW fibrinogen or depleted in LMW fibrinogen. Usually, the test kit will also comprise an enzyme suitable for forming fibrin from fibrinogen, such as thrombin, and optionally factor XIIIa and/or $CaCl_2$. The enzyme will, if present, normally be present in a separated container to prevent preliminary conversion of the fibrinogen. Also, the test kit will comprise components for effecting angiogenesis. The test kit will comprise as components for effecting angiogenesis one or more angiogenesis growth factors, such as fibroblast growth factor-2 (FGF-2) or vascular endothelial growth factor (VEGF), and/or tumor necrosis factor alpha (TNF-α), and/or cells, such as human endothelial cells.

Summarizing, the following applications of the present invention may be mentioned.

tissue engineering: the modulation of the characteristics of the fibrin-containing matrix in relation to cell growth, for instance optimization of the fibrin-containing matrix for an accelerated angiogenesis (for instance fibrin sealants, wound healing, burns), for instance by using fibrinogen enriched in the HMW fibrinogen form.

tissue engineering: the modulation of the characteristics of the fibrin-containing matrix in relation to cell growth, for instance optimization of the fibrin-containing matrix for an decelerated angiogenesis (for instance inhibition of growth of tumors, fibrin sealants), for instance by using fibrinogen enriched in the LMW fibrinogen form.

the acceleration of the in vitro angiogenesis tests, which, during use of the total fibrinogen, now take 7 days. Accelerated ingrowth of blood vessels in the fibrin matrix, for instance by using HMW fibrinogen, results in a substantial acceleration of the in vitro tests, so that they take less time.

the promotion or inhibition of cell growth on a fibrin-containing matrix, for instance to inhibit and most preferably prevent scar growth, adhesions and the like.

the modulation in vivo of the HMW fibrinogen/LMW fibrinogen ratio with the purpose of allowing the formation of a fibrin matrix in which cell growth is stimulated or inhibited. This could be done, for instance, within the scope of a treatment of post-thrombotic syndrome (open leg). The intended modulation of the HMW/LMW fibrinogen ratio could be realized by stimulating or inhibiting the conversion of HMW to LMW, for instance by adding one or several of the enzymes effecting this conversion or a suitable antagonist. Also, the endogenic production of a respective enzyme could be stimulated or inhibited.

EXAMPLES

The in vitro angiogenesis model used in the following examples is based on the ingrowth of human prepuce microvascular endothelial cells (hMVEC) in a 3-dimensional fibrin matrix (besides, prepuce microvascular endothelial cells of other mammals may also be used). After seeding the hMVEC in a confluent monolayer on top of the fibrin matrix, these hMVEC can be stimulated to invading the fibrin matrix in which blood vessel-like structures are formed. This vessel formation takes place after stimulation of the hMVEC with angiogenic growth factors, such as fibroblast growth factor-2

(FGF-2) or vascular endothelial growth factor (VEGF), in combination with the inflammation mediator tumor necrosis factor α (TNFα).

Electron microscopic analysis of the invasive capillary, structures makes it clear that the fibrin structure, in addition to the ingrown cells, is partly broken down, which indicates that the proteolytic processes are involved in the cell invasion, in particular the cell-bound u-PA and plasmin activity. (Koolwijk et al., J. Cell Biol. 132: 1177-1188, 1996).

These experiments have been carried out, inter alia, with commercially obtained human fibrinogen. This fibrinogen consists of a mixture of the HMW, LMW and LMW' forms. When using this fibrinogen mixture, the onset of vessel formation begins after about 3 days and the amount of blood vessel-like structure can be measured reliably after 7-10 days by means of an image analysis system (Koolwijk et al., J. Cell Biol. 132: 1177-1188, 1996).

Also, experiments were carried out with HMW-enriched and LMW-enriched fibrinogen.

Culture Conditions of Human Endothelial Cells

Human prepuce microvascular endothelial cells (hMVEC) were isolated and cultured in fibronectin-coated or gelatin-coated culture plates in medium M199 (Biowitthaker, Verviers, Belgium; described in Morgan, Morton and Parker, Proc. Soc. Exptl. Biol. Med. 73: 1-8, 1950), 2 mM L-glutamine, 20 mM HEPES (pH 7.3) (Biowitthaker, Verviers, Belgium), 10% heat-inactivated human serum (serum pooled from 15-20 donors, obtained from a local blood bank), 10% heat-inactivated newborn calf serum (Invitrogen, Paisley, Scotland), 150 μg/mL crude endothelial cell growth factor supplement (ECGFs) (prepared from bovine brain), 5 U/mL heparin (Leo Pharmaceutical Products, Weesp, The Netherlands), 100 IU/mL penicillin and 100 μg/mL streptomycin (Biowitthaker)). Passage 10 cells were used for the in vitro angiogenesis and cell growth experiments.

For the cell growth experiments confluent endothelial cells (MVEC) were detached from 1% gelatin-coated plastic culture flasks using 0.05% trypsin/1 mmol/L EDTA and cultured in M199 medium, supplemented with 100 IU/ml penicillin, 100 μg/ml streptomycin, 10% human serum, 10% newborn calf serum, 0.1% heparin and 0.75% (w/v) ECGF.

Culture Conditions of Human Smooth Muscle Cells

Human left internal mammary artery smooth muscle cells (HSMC) were isolated as described by Negre-Aminou et al. (Biochim. Biophys. Acta 1997; 1345: 259-268). Confluent cells were detached from plastic culture flasks using 0.125% trypsin/2.5 mmol/l EDTA and cultured in DMEM medium supplemented with 100 IU/ml penicillin, 100 μg/ml streptomycin, 10% fetal calf serum and 10% human serum.

Culture Conditions of Human Cornea Fibroblasts

Human cornea fibroblasts were isolated as described by Negre-Aminou et al. (Biochim. Biophys. Acta 1997; 1345: 259-268). Confluent cells were detached from the plastic culture bottle using 0.125% trypsin/2.5 mmol/l EDTA cultured in DMEM, 100 IU/ml penicillin, 100 μg/ml streptomycin and 10% fetal calf serum.

In Vitro Endothelial Cell Growth

The endothelial cells (MVEC) were detached from culture wells using trypsin/EDTA and directly seeded (70% confluency) on the fibrin matrix. After 48 hours, pictures were taken of the cells for the visual assessment of the condition and quantity of the cells.

Figure 3:
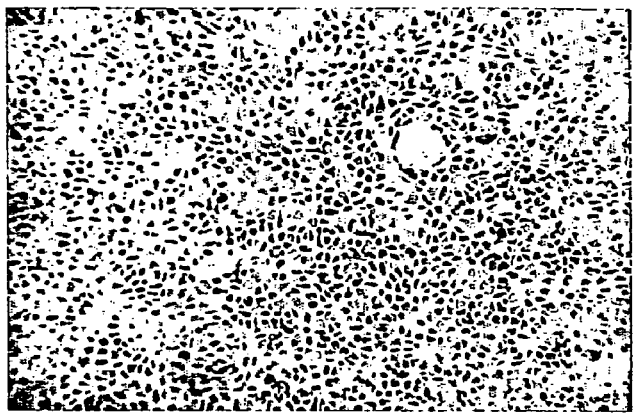
FIG. 3 shows the effect of variation of fibrinogen type on endothelial cell growth on a fibrin matrix. The upper photograph pertains to a fibrin matrix made of 100% HMW fibrinogen The photograph in the middle relates to a fibrin matrix made of 70% HMW+30% LMW fibrinogen. The lower photograph relates to a fibrin matrix made of 60% HMW+40% LMW fibrinogen.
Figure 3:
Figure 3:

The results are shown in FIG. 3. On fibrin matrices made of 100% HMW fibrinogen, endothelial cells grow faster than on fibrin matrices made of 70% HMW+30% LMW fibrinogen, and the growth is less on fibrin matrices made of 60% HMW+40% LMW fibrinogen.

In Vitro Smooth Muscle Cell Growth

The smooth muscle cells were detached from culture wells using trypsin/EDTA and directly seeded (70% confluency) on the fibrin matrix. After 48 hours, pictures were taken of the cells for the visual assessment of the condition and quantity of the cells.

Figure 4:
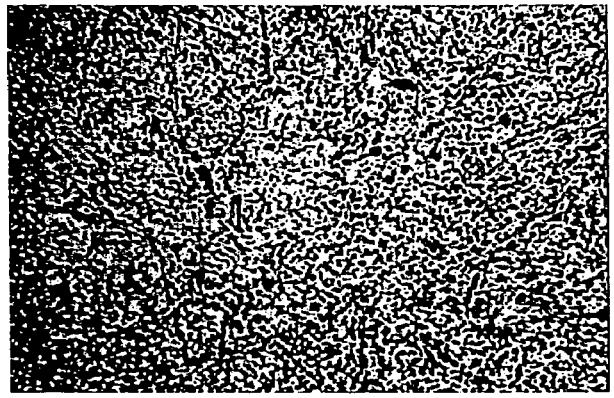
FIG. 4 shows the effect of variation of fibrinogen type on smooth muscle cell growth on a fibrin matrix. The upper photograph pertains to a fibrin matrix made of 100% HMW fibrinogen. The photograph in the middle relates to a fibrin matrix made of 70% HMW+30% LMW fibrinogen. The lower photograph relates to a fibrin matrix made of 50% HMW+50% LMW fibrinogen.
Figure 4:
Figure 4:

The results are shown in FIG. 4. On fibrin matrices made of 100% HMW fibrinogen, smooth muscle cells grow faster than on fibrin matrices made of 70% HMW+30% LMW fibrinogen, and the growth is less on fibrin matrices made of 60% HMW+40% LMW fibrinogen.

In Vitro Fibroblast Growth

The fibroblasts were detached from culture wells using trypsin/EDTA and directly seeded (70% confluency) on the fibrin matrix. After 48 hours, pictures were taken of the cells for the visual assessment of the condition and quantity of the cells.

Figure 5:
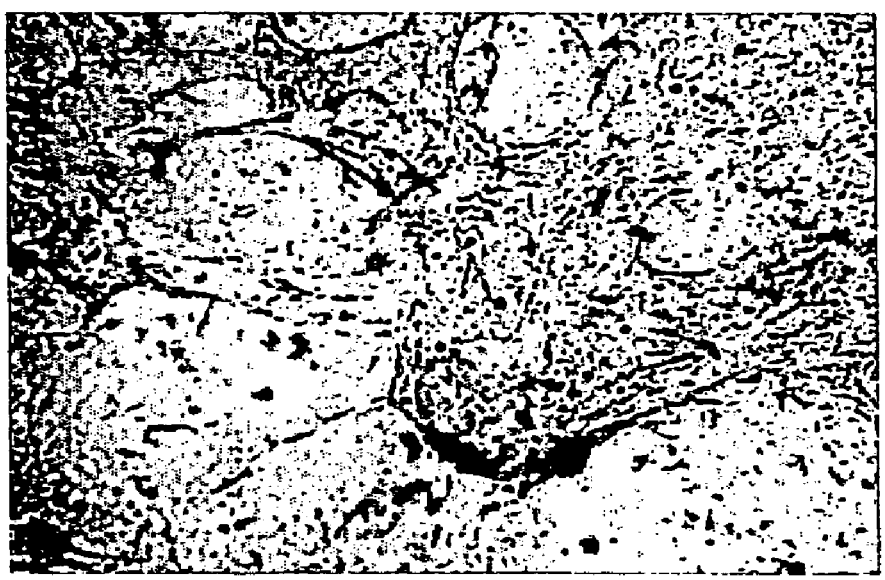
FIG. 5 shows the effect of variation of fibrinogen type on fibroblast cell growth on a fibrin matrix. The upper photograph pertains to a fibrin matrix made of 100% HMW fibrinogen. The lower photograph relates to a fibrin matrix made of 70% HMW+30% LMW fibrinogen.
Figure 5:

The results are shown in FIG. 5. On fibrin matrices made of 100% HMW fibrinogen, fibroblast degrade the matrix after 48 hours, while on fibrin matrices made of 70% HMW+30% LMW fibrinogen, the cells stretch out nicely and grow without degradation of the matrix until at least day 7.

Purification of HMW and LMW Fibrinogen

From total fibrinogen (purified from plasma according to the method by Van Ruyven-Vermeer & Nieuwenhuizen, Biochem. J. 169: 653-658, 1978; or commercially obtained) the HMW, LMW and LMW' forms of fibrinogen are purified.

Fibrinogen is dissolved/dialyzed in a physiological buffer, such as Owren buffer or a Tris/HCl buffer (10 mM Tris/HCl, pH 7.4). To this is slowly added $(NH_4)_2SO_4$ up to a final concentration of 19%. The thus obtained solution is mixed for 15-30 minutes at room temperature and then centrifuged for 10 min at 2500 rpm. The pellet is included in the start volume buffer (37° C. while carefully swinging) and the 19% $(NH_4)_2SO_4$-precipitation step is carried out once again. After this step, the pellet contains pure HMW (±99% pure), which is included in buffer again.

To the supernatant of the first precipitation step is added $(NH_4)_2SO_4$ up to a final concentration of 22%. After mixing and centrifuging, the supernatant is collected. To this is now added $(NH_4)_2SO_4$ up to a final concentration of 24%, after mixing and centrifuging the pellet is included in buffer. This pellet contains pure LMW fibrinogen (±95% pure).

To the supernatant is added $(NH_4)_2SO_4$ up to a final concentration of 24%. After mixing and centrifuging, the supernatant is collected. To this is now added $(NH_4)_2SO_4$ up to a final concentration of 27%, after mixing and centrifuging the pellet is included in buffer. This pellet contains pure LMW' fibrinogen (±95% pure).

The solutions with HMW, LMW en LMW' fibrinogen are then dialyzed (against PBS or M199), checked for purity by SDS-PAGE under non-reducing conditions, the concentration is determined by measuring the extinction at 280 nm, and the preparations were stored at −80° C. for use in the angiogenesis experiments.

Purification of Other Forms of Fibrinogen

Fibrinogen from volunteers and/or patients with a specific genotype or an increased/reduced concentration of a variant fibrinogen (see Table) is purified according to the method by Van Ruyven-Vermeer & Nieuwenhuizen, Biochem. J. 169: 653-658, 1978. The purified fibrinogen is then dialyzed (against PBS or M199), checked for purity by SDS-PAGE under non-reducing conditions, the concentration is determined, for instance by measuring the extinction at 280 nm and the preparations are stored at −80° C. for use in the angiogenesis experiments.

Preparation of the Fibrin Gels

Three-dimensional human fibrin matrices were prepared by adding 2 μl of a 100 U/ml thrombin solution to 100 μl of a 2 mg/ml fibrinogen solution in M199. In some experiments was added factor XIIIa with 5 mm $CaCl_2$. After 1 hour of polymerization, the thrombin was inactivated by incubating the matrices for 2-4 hours with 0.2 mL M199 with 10% human serum and 10% newborn calf serum. All experiments were carried out at least in duplicate.

In Vitro Angiogenesis Assay

The endothelial cells were detached from the fibronectin-coated or gelatin-coated culture plates by means of trypsin/EDTA and directly confluently seeded on the fibrin matrices. After 24 hours, and subsequently always after 48 hours, the endothelial cells were stimulated with M199, 10% human serum, 10% newborn calf serum, 10 ng/ml bFGF and 10 ng/ml TNFa. The formation of vessel-like structures of endothelial cells by invasion of the subjacent matrices was analyzed by means of phase contrast microscopy (Koolwijk et al., J. Cell Biol. 132: 1177-1188, 1996).

FIG. 1 shows the effect of variation of fibrinogen type on vessel ingrowth in the fibrin matrix formed. On fibrin matrices, made with unfractionated fibrinogen, the hMVEC do not grow in under control (non-stimulated) conditions (photos A and E). If stimulated with a combination of bFGF and TNFa, after about 3 days "onsets" of vessel formation are visible (see arrows in photo B), which after 7 days were grown out to vessel-like structures large enough to be measured by means of a video camera, mounted on a reversing microscope, and by means of an image analysis program (photo F). Cross-sections of these vessel-like structures show that these structures contain a lumen, surrounded by endothelial cells (results not shown). If the hMVEC on fibrin matrices, made with purified HMW fibrinogen, are seeded, then it is visible that the ingrowth of the hMVEC takes place much faster. After 3 days of stimulation with bFGF and TNFa, large vessel-like structures are already detectable, which at that moment can be excellently measured by means of the image analysis apparatus (photo C). After 7 days, so many ingrowing hMVEC are already visible that this can no longer be properly measured with the image analysis apparatus (photo G). All that is in contrast with what is found when the matrices are made with purified LMW fibrinogen. The hMVEC then no longer form vessel-like structures after 3 and 7 days (photos D and H), nor after 10 days of stimulation (data not shown).

Figure 2:
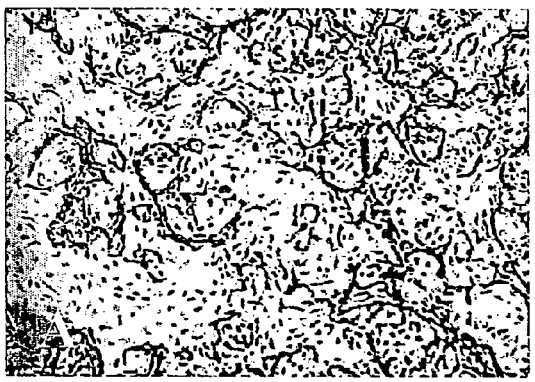
FIG. 2 contains photos A-D, showing the results after 7 days of testing, whereby human microvascular endothelial cells (hMVEC) were seeded on a three-dimensional fibrin matrix, made of 100% HMW fibrinogen (photo A), 90% HMW+10% LMW fibrinogen (photo B), 80% HMW+20% LMW fibrinogen (photo C) or 60% HMW+40% LMW fibrinogen (photo D) and stimulated with a combination of bFGF and TNFα. The photos are representative of 3 different experiments.
Figure 2:
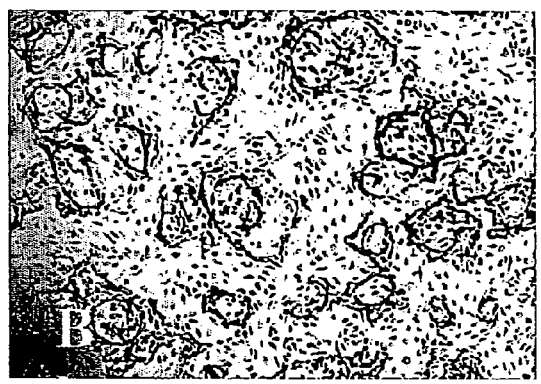
Figure 2:
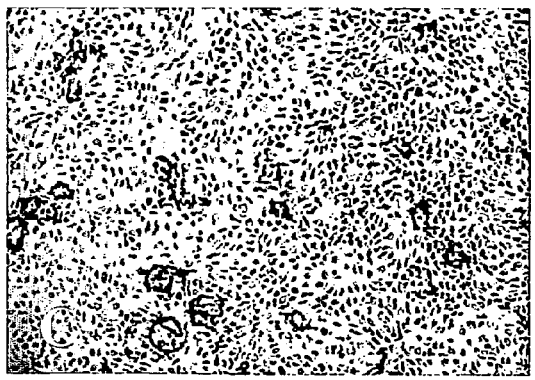
Figure 2:
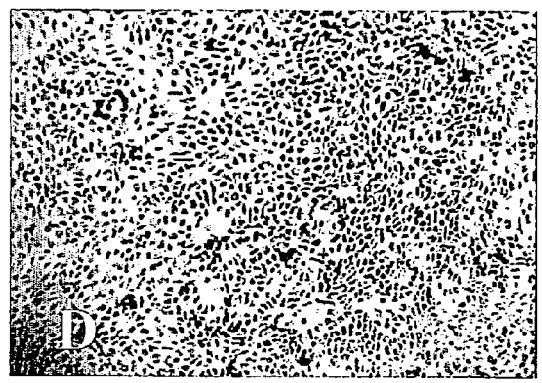

FIG. 2 shows the effect of the amount of LMW fibrinogen on vessel ingrowth in fibrin matrices made of HMW fibrinogen. On fibrin matrices made of 100% HMW fibrinogen, very many ingrowing, vessel-forming hMVEC are visible after a stimulation period of 7 days (photo A). According as more LMW fibrinogen is added during the coagulation of the matrices, the hMVEC can form fewer vessel-like structures. At a ratio of 60% HMW and 40% LMW, it is visible that practically no vessel ingrowth occurs anymore (photo D).

Results

In the experiments described, it was found that the heterogeneity in naturally occurring fibrinogen influences the ingrowth of blood vessels in the fibrin matrix (in in vitro angiogenesis). Thus the hMVEC appear to show an accelerated ingrowth in a fibrin matrix formed from the HMW form of fibrinogen relative to the total (unfractionated, mixed) fibrinogen. When the vessel ingrowth in fibrin matrices formed from the LMW form of fibrinogen was considered, it appeared that it no longer took place at all. Even after 10 days of stimulation, it appeared that no vessel-like structure was formed.

When the fibrin matrix was made of a mixture of HMW and LMW fibrinogen, it was clear that the greater the percentage of LMW fibrinogen, the less fast the angiogenesis took place. In a matrix made of 60% HMW/40% LMW fibrinogen, a vessel-like structure was hardly visible after 7 days.

TABLE

Naturally occurring fibrinogen variants

| fibrinogen variant | |
|---|---|
| genetic polymorphisms leading to another protein | T/A312 polymorphism in the fibrinogen alpha gene and the R/K448 polymorphism in the fibrinogen beta gene |
| variation in phosphorylation | Fibrinogen circulates with different degree of phosphorylation, particularly in newborns an increased phosphorylation level is found |
| glycosylation/ sialic acid | Fibrinogen circulates with different degree of glycosylation, particularly during an acute phase reaction. |
| gamma' | Fibrinogen in which in the COOH-terminal gamma-chain peptide the last four amino acids are replaced by a 20-residue fragment rich in aspartic and glutamic acid, with the sequence Val-Arg-Pro-Glu-His-Pro-Ala-Glu-Thr-Glu-Tyr-Asp-Ser-Leu-Tyr-Pro-Glu-Asp-Asp-Leu |
| Fib420 | Fibrinogen with extended α-chain (αE) chain, molecular weight ± 420 kDa, in healthy persons ±5% of the total circulating fibrinogen |
| HMW | High-molecular weight fibrinogen with both Aα-chains intact, the form in which fibrinogen is synthesized, in healthy persons ±70% of the total circulating fibrinogen |
| LMW | Low-molecular weight fibrinogen with one Aα-chain intact and one partly broken down, in healthy persons ±26% of the total circulating fibrinogen |
| LMW' | Low-molecular weight fibrinogen with both Aα-chains partly broken down, in healthy persons ±4% of the total circulating fibrinogen |

The invention claimed is:

1. A method for accelerating angiogenesis in a patient comprising: topically administering to the patient, at a site where angiogenesis acceleration is desired, a fibrin matrix made by the process of forming the fibrin matrix from a composition comprising fibrinogen and a pharmaceutically acceptable carrier, wherein the fibrinogen has a high molecular weight (HMW) content of at least 80% (w/w) of the total fibrinogen amount.

2. The method of claim 1, where wherein the high molecular weight fibrinogen content is a mixture enriched in the Fib420 form of fibrinogen.

3. The method of claim 1 where the fibrin matrix is applied to burnt tissue of a patient.

4. The method of claim 1 where the fibrin matrix is applied to wounded tissue of the patient.

5. The method of claim 1 where the fibrin matrix is applied to an internal organ of the patient during a surgical procedure.

6. The method of claim 1, wherein the composition further contains one of more of factor XIIIa, $CaCl_2$ or an enzyme capable of forming fibrin from fibrinogen.

7. The method of claim 6, where the enzyme is thrombin.

8. A method for decelerating angiogenesis in a patient comprising: topically administering to the patient, at a site where angiogenesis deceleration is desired, a fibrin matrix made by the process of forming a fibrin matrix from a composition comprising fibrinogen and a pharmaceutically acceptable carrier, wherein the fibrinogen has a low molecular weight content (LMW) of at least 40% (w/w) of the total fibrinogen amount.

9. The method of claim 8, where wherein the low molecular weight fibrinogen content is a mixture enriched in the gamma form of fibrinogen.

10. The method of claim 8, wherein the composition further contains one of more of factor XIIIa, $CaCl_2$ or an enzyme capable of forming fibrin from fibrinogen.

11. The method of claim 10, where the enzyme is thrombin.

12. The method of claim 8 where the composition is topically administered to an internal organ of a patient during the course of a surgical procedure.

13. The method of claim 8 where the composition is applied to a wound of a patient to lessen scar formation or adhesions of the wound.

* * * * *